(12) United States Patent
Maffei (10) Patent No.: US 7,086,563 B2
(45) Date of Patent: Aug. 8, 2006

(54) DISPENSING CARTON FOR BANDAGES AND THE LIKE

(75) Inventor: Camilla Maffei, Pistoia (IT)

(73) Assignee: Projects S.a.s. di Massimo Memichelli & C. (IT)

( * ) Notice: Subject to any disclaimer, the term of this patent is extended or adjusted under 35 U.S.C. 154(b) by 256 days.

(21) Appl. No.: 10/478,607

(22) PCT Filed: May 20, 2002

(86) PCT No.: PCT/IT02/00329

§ 371 (c)(1),
(2), (4) Date: Nov. 20, 2003

(87) PCT Pub. No.: WO02/094686

PCT Pub. Date: Nov. 28, 2002

(65) Prior Publication Data

US 2004/0149771 A1    Aug. 5, 2004

(30) Foreign Application Priority Data

May 23, 2001    (IT)    .......................... PT20010005 U (51) Int. Cl.
*A47F 1/04*    (2006.01)
*G07F 11/16*    (2006.01)
(52) U.S. Cl. ..................................... 221/305; 221/309
(58) Field of Classification Search ................ 221/232,
221/46, 45, 63, 49, 305, 60, 39.5, 35, 34,
221/130, 131, 309; 206/440, 525.1, 441;
229/120, 120.12
See application file for complete search history.

(56) References Cited

U.S. PATENT DOCUMENTS

| 1,173,843 | A | * | 2/1916 | Morten ...................... 206/39.3 |
| 3,333,690 | A | * | 8/1967 | Marsh ........................ 206/554 |
| 3,392,903 | A | * | 7/1968 | Morgan, Jr. ............. 206/45.21 |
| 3,456,862 | A | * | 7/1969 | Stegner .................. 229/120.17 |
| 4,350,281 | A | * | 9/1982 | Dornbusch et al. ......... 206/774 |
| 5,458,236 | A | * | 10/1995 | Schoettle et al. ........... 206/232 |
| 5,509,570 | A | * | 4/1996 | DeMatteis ................... 221/33 |
| 5,924,559 | A | * | 7/1999 | Carrel et al. ............. 206/45.21 |
| 5,971,261 | A | * | 10/1999 | Grunfeld et al. ............ 229/102 |
| 6,050,449 | A | * | 4/2000 | Kanj .......................... 221/232 |
| 6,053,325 | A | * | 4/2000 | Yonker et al. .............. 206/736 |
| 6,079,190 | A | * | 6/2000 | Simpson ...................... 53/492 |
| 6,554,159 | B1 | * | 4/2003 | Behr et al. .................. 221/305 |
| 6,592,003 | B1 | * | 7/2003 | Silverthorne ................ 221/60 |

\* cited by examiner

*Primary Examiner*—Kathy Matecki
*Assistant Examiner*—Rakesh Kumar
(74) *Attorney, Agent, or Firm*—McGlew and Tuttle, PC (57) ABSTRACT

The parallelepiped-shaped carton made of paperboard or the like, for packaging and dispensing bandages or other products, comprises in at least one B of the two main faces one or two windows B1, B2 and in the internal volume of the carton a wall F with a sloping surface relative to said main face; said wall and said face define a slot K1, through which an individual product can be slid out in direction W1, by acting on it through said window.

14 Claims, 7 Drawing Sheets

DISPENSING CARTON FOR BANDAGES AND THE LIKE

Cartons of various sizes, usually made of paperboard, containing bandages of different shapes (rectangular, round, etc.). dimensions and colors for covering and protecting small flesh wounds and abrasions are available on the market These cartons may also contain bandages of different kinds, such as bandages made of nonwoven material (or other material), wrappings for individual hygienic protective covers for physicians' stethoscopes individual wrappings for tongue depressors and individual wrappings for spatulas and cervical brushes for gynaecological use. Similar cartons may also contain other products, or other thin objects having at least moderate resistance to bending, due in part to the individual protection provided for each object. For simplicity, references below will be to bandages.

The use of (individually wrapped) bandages of any kind, shape and size has become routine in clinical and hospital work, in physicians' bags and also in first-aid kits for homes, schools and cars.

The revelent background art is disclosed in the documents DE 1225541B (corresponding to the preamble of claim 1) and U.S. Pat. No. 3,370,7764A (dispense with two dispensing openings).

The invention described below modifies the cartons containing the bandages or other objects, In such a way as to achieve a number of advantages, the primary one being to make it possible to use the carton without having to open it to extract a bandage. The carton thus becomes a dispensing carton.

The dispensing carton that forms the subject-matter of the invention also allows the user to select from the outside what type of bandage is to be removed. The carton can, for example, dispense bandages all of the same size (or all of the same kind) or of two or three different sizes, kinds and/or shapes. The user can immediately see from the outside how many and what sort of bandages are still available for use. With ordinary cartons, on the other hand, the pack has to be opened, and in order to find one suitable for the immediate need, it is often necessary to tip the entire contents out and, after selecting the bandage, put all the rest back into the package.

The dispensing carton of the invention can be produced from die cut paperboard blanks and ordinary "fold and stick" gluing lines and can therefore be produced industrially in the same way as cartons that are already commercially available.

In essence, the carton in question, which is parallelepiped-shaped and made of paperboard or the like, for packaging and dispensing products such as those listed above, comprises in at least one of the two main faces a window and in the internal volume of the carton a wall with a sloping surface relative to said main face; said wall and said face define a slot through which an individual product can be slid out by acting on it through said window.

In one advantageous embodiment, the carton, especially where intended for packaging and dispensing products such as adhesive bandages or the like, comprises in each of the two main faces at least one window and in the internal volume of the carton a separator forming two sloping surfaces relative to said two main faces, each of said surfaces defining with the corresponding face a respective seat for the products and a slot, through which an individual product can be slid out by acting on it through the corresponding window.

In practice the carton may comprise in each of the two main faces at least one window and in the internal volume of the carton a separator that slopes relative to said two main faces, which defines with said two faces two respective opposite seats for products and two opposite slots, through each of which an individual product can be slid out by acting on it through the corresponding window.

Said separator may take the form of a continuation of one of the two faces at right angles to the slots.

The carton may comprise, on at least one of the main faces, two adjacent and aligned windows and in this case it comprises an internal divider between the two windows, so as to form two separate spaces for different products to be pushed out through the respective slot. Said internal divider may consist of two extensions extending from two opposite edges perpendicular to one of the two faces and to one of the slots, which extensions are folded along the wall of the carton contiguous with the slot and also internally to form said internal divider and define said two separate spaces.

A clearer understanding of the invention will be gained from the description and attached drawing, the latter showing a practical, non-limiting example of said invention. In the drawing.

The enclosed drawings show a non-limiting example of the invention.

Figure 1:
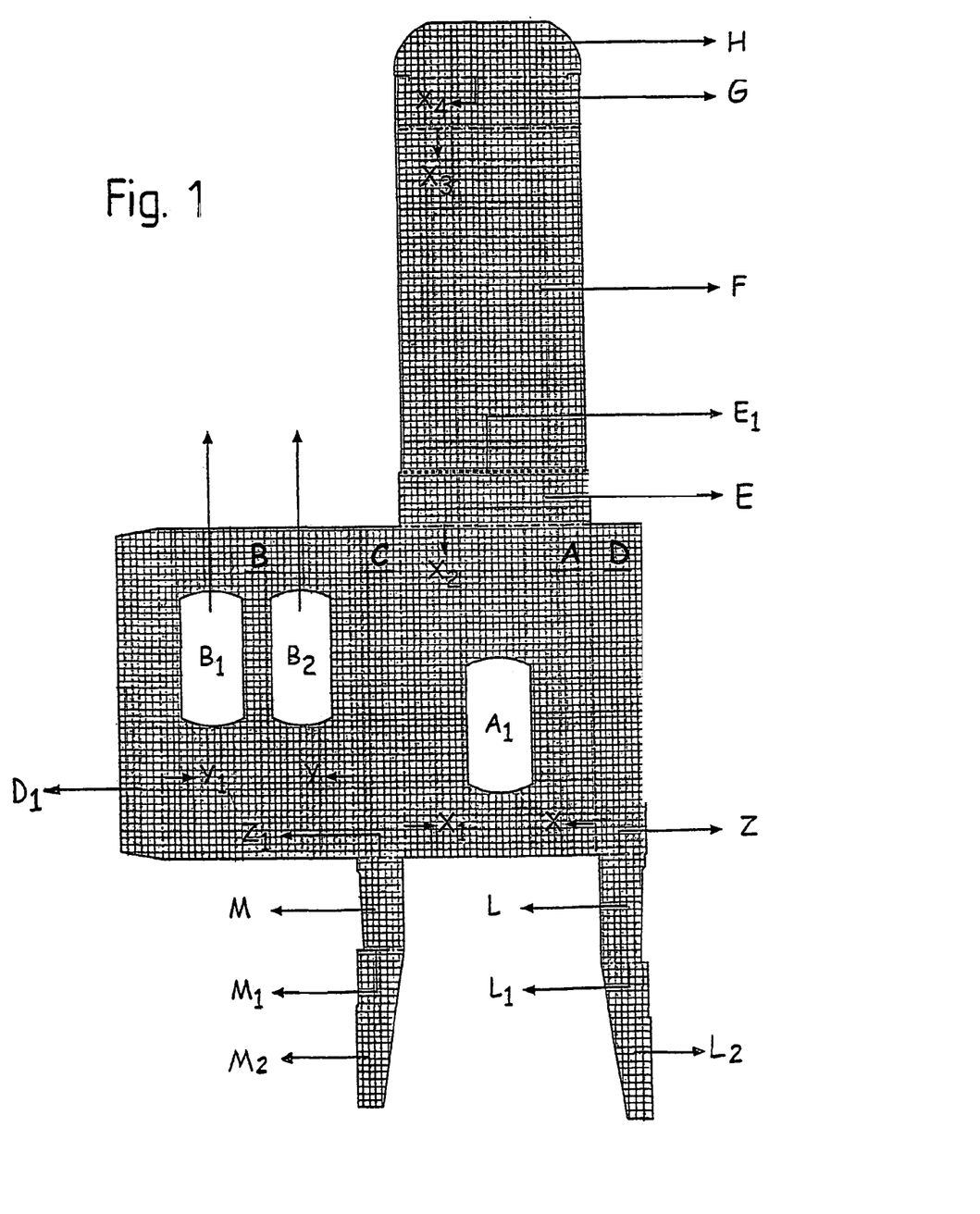
FIG. 1 shows the opened-out form of a blank for forming a three-volume carton for products to be individually packaged and removed.

FIG. 1 shows the inside of the opened-out form of a carton for two or three sizes of bandages, before it is folded and glued to form the dispensing carton.

Letters A and B indicate the two main faces, face A defined by fold lines, that is score lines X, X1 and X2 and face B by score lines Y and Y1. Face A has a window A1 and face B may have a single window or two windows B1 and B2. Beyond score line X lies a long side D, and between score lines X1 and Y a long side C; beyond score line Y1 is a tab D1; beyond score line X2 is a short side E, which is also bounded by a half-cut fold line E1, from which extends a separator F aligned with face A and defined by a score line X3, which last, together with a further score line X4 defines a carton wall G opposite the short side E; and beyond score line X4 extends a tab H.

If the carton is designed to contain three sizes of bandage (or the like), there are two windows B1, B2 in face B and in this case there are two shaped extensions L and M that begin at fold lines Z, Z1, respectively, defining the long sides D and C. Each of said extensions L and M is divided by a fold line L1, M1, respectively, that defines a continuation L2, M2, respectively, designed to create an internal divider.

Figure 2:
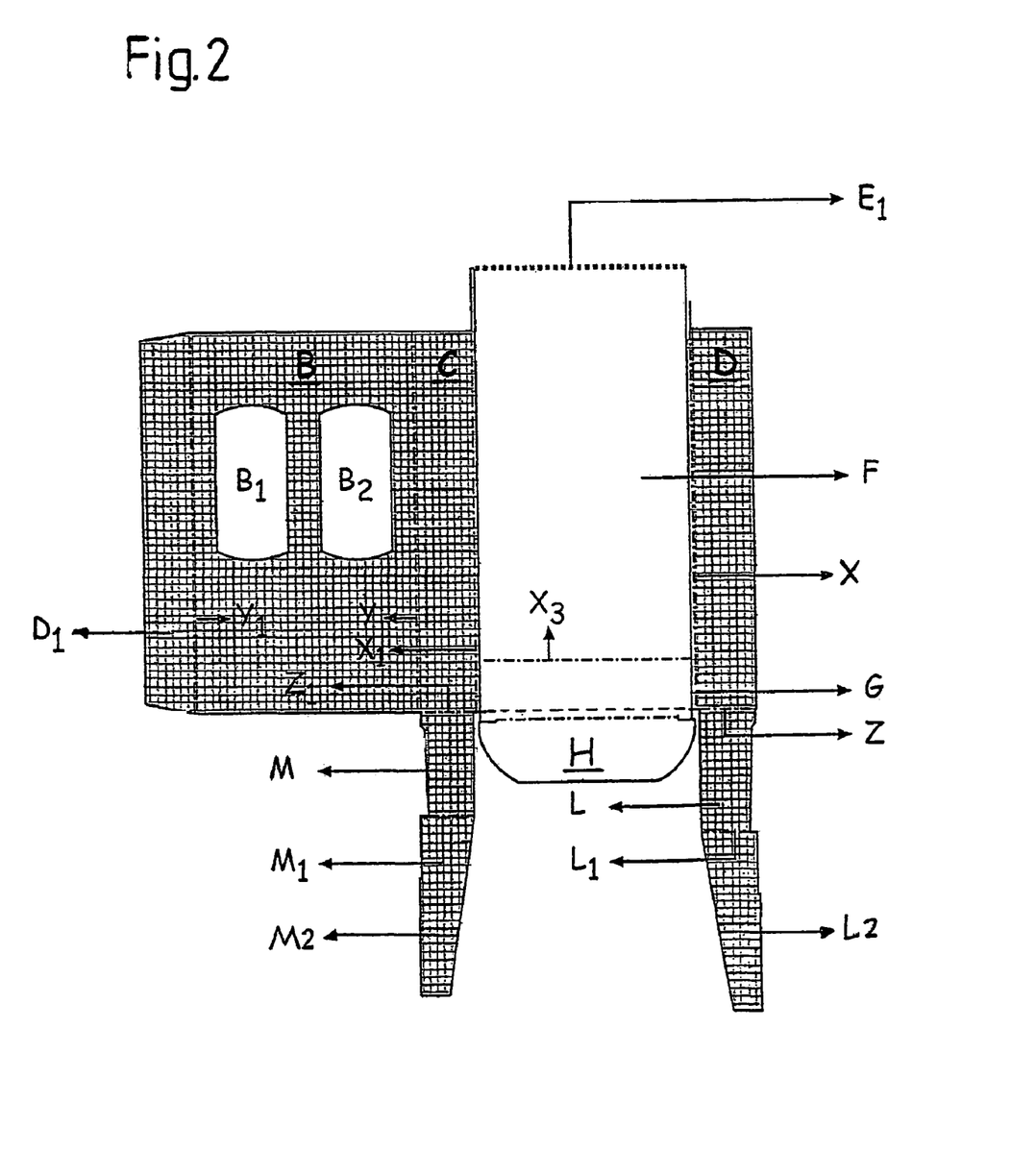
FIGS. 2, 3 and 4 show three stages in the forming of the carton.
Figure 3:
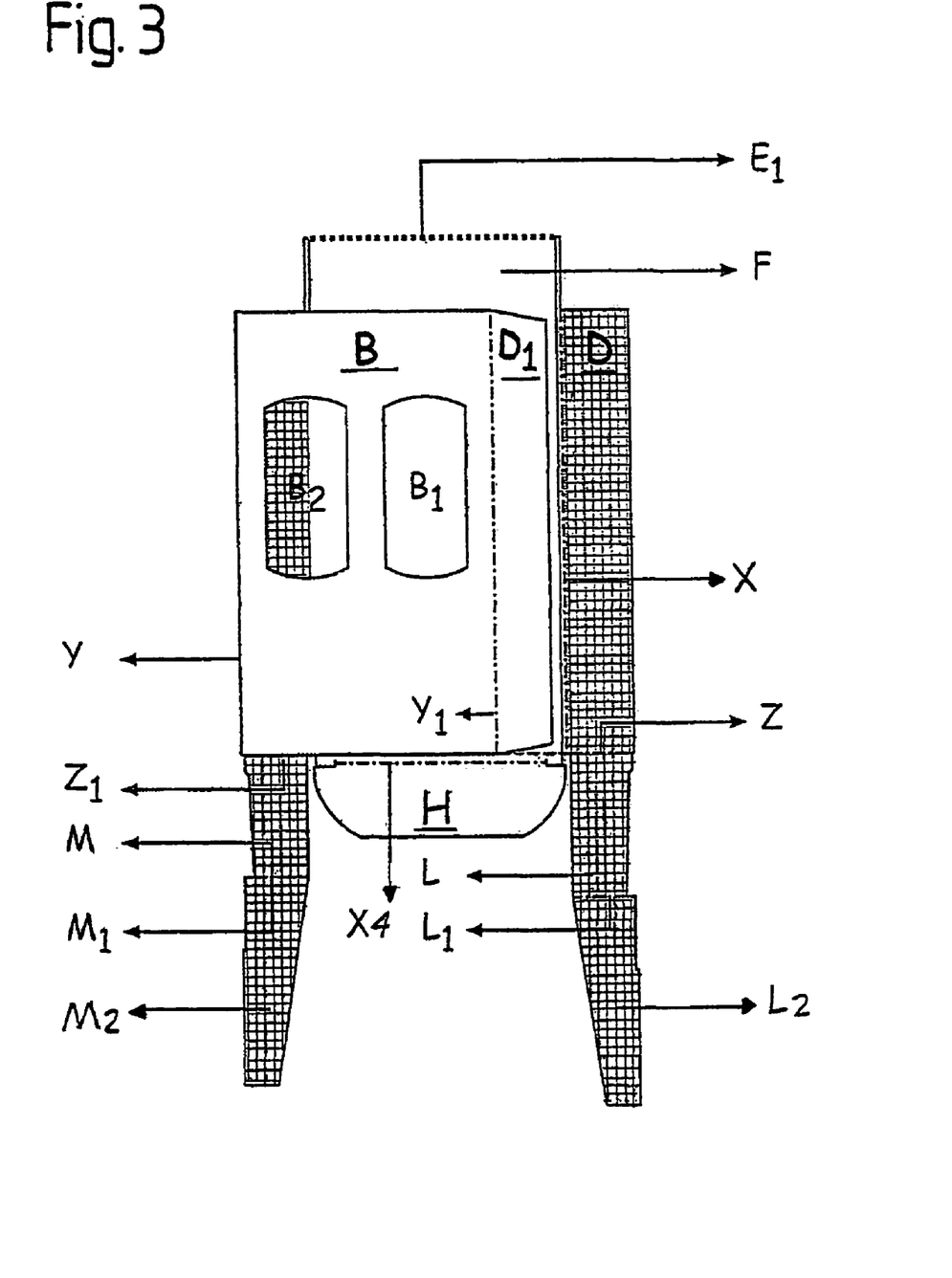
Figure 4:
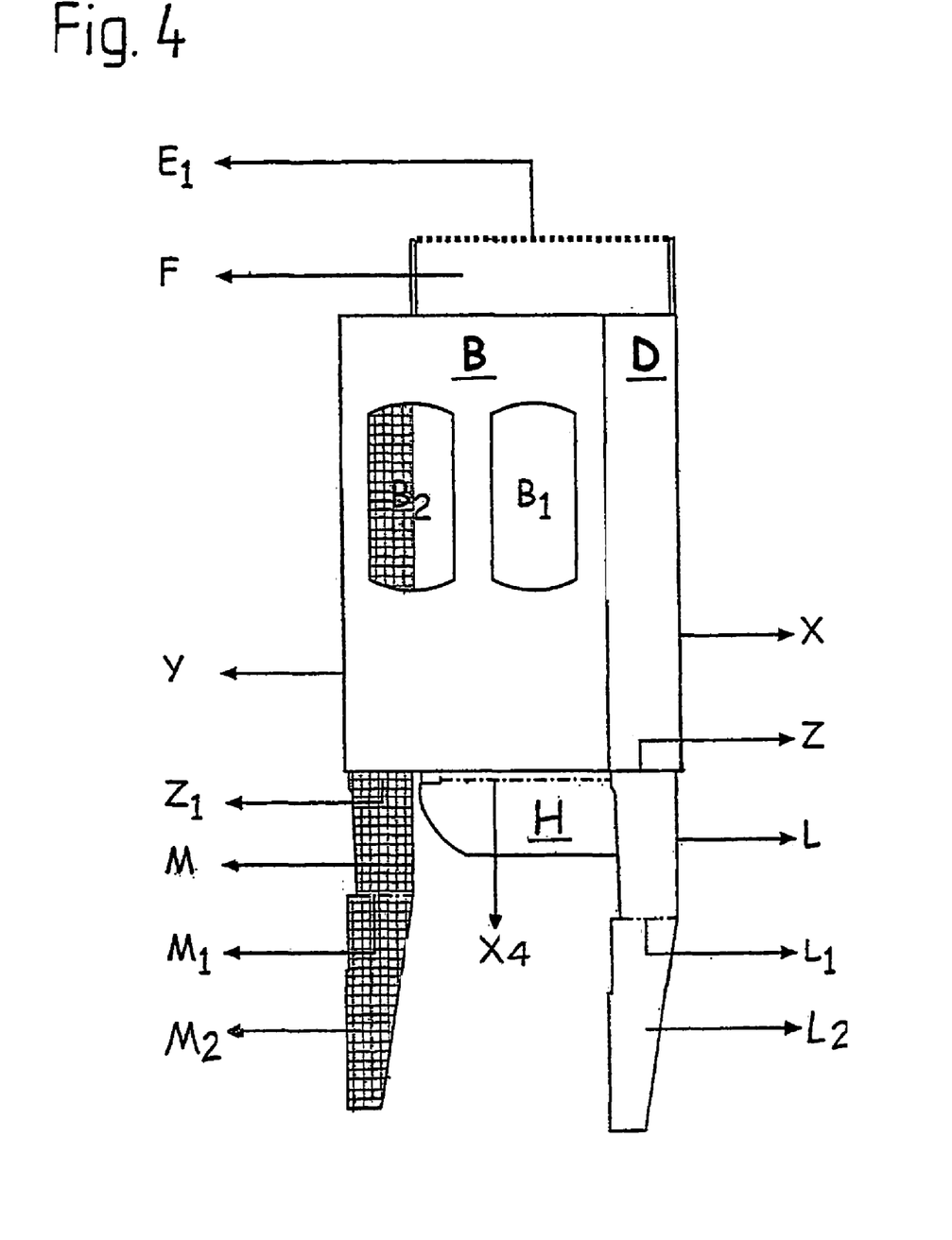

With this morphology of the opened-out form as shown in FIG. 1, the separator F is first folded, by means of the half-cut line E1, so as to touch the inside of face A of the carton (see FIG. 2). Score line Y (FIG. 3) is then folded, followed by score line X (FIG. 4) so as to glue side D to tab D1 (FIG. 4). The dispensing carton will thus be formed by six sides A, B, C, D, E, and G and can assume its parallelepiped shape, with the separator F contained inside the carton. The windows A1 (on side A) and B1, B2 (on side B) will allow bandages to be pushed out one at a time, as explained below. The carton is completed in its three-dimensional aspect.

Figure 5:
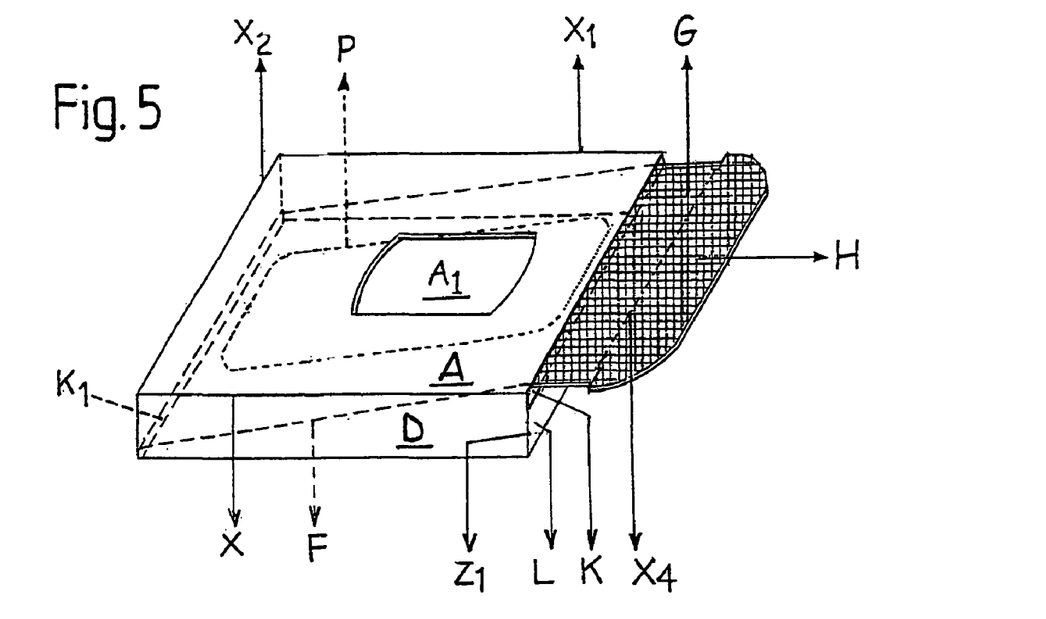
FIGS. 5 and 6 show two opposite perspective views of the carton, which is about to undergo the final stage in its formation.
Figure 6:
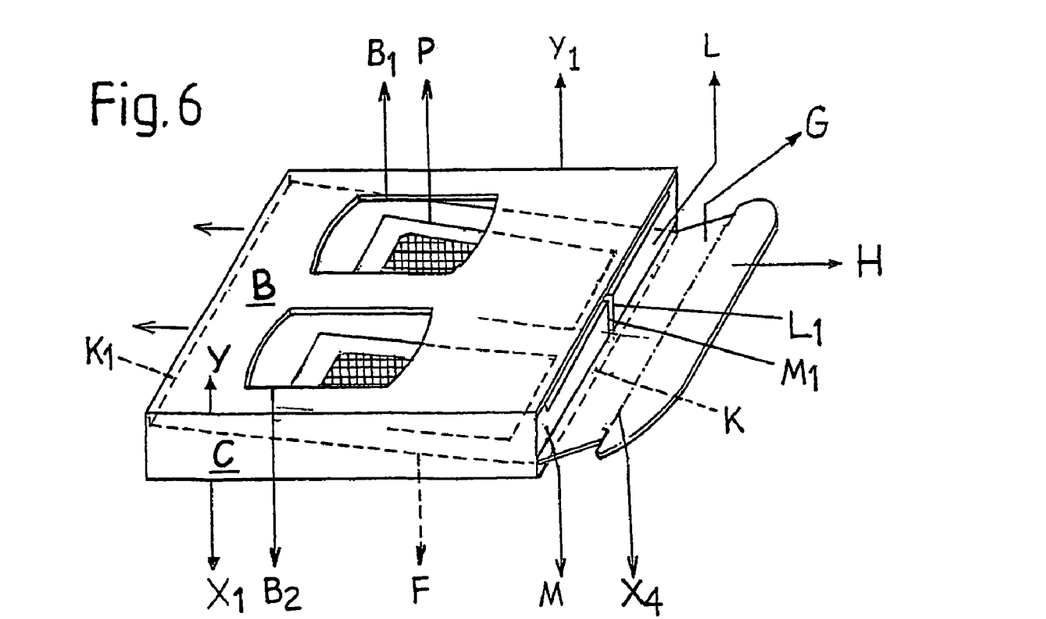
Figure 7:
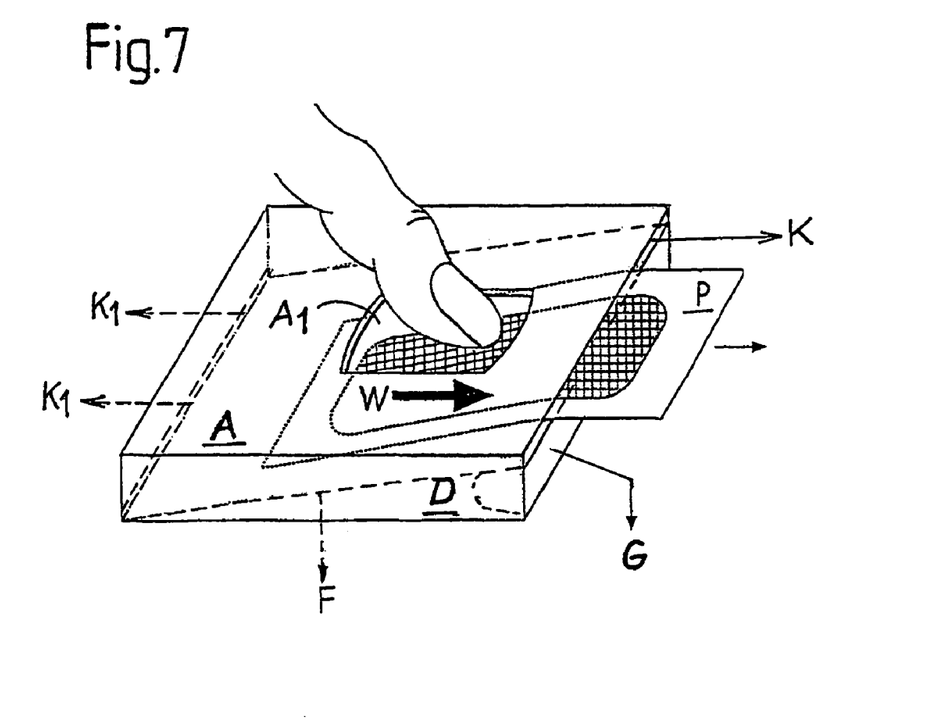
FIGS. 7 and 8 show two perspective views illustrating two dispensing operations.
Figure 8:
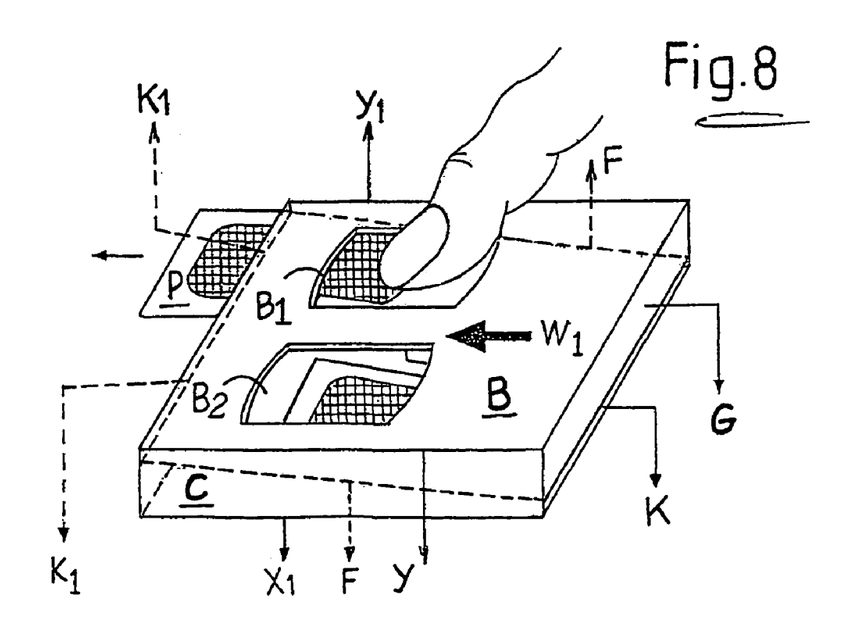
Figure 9:
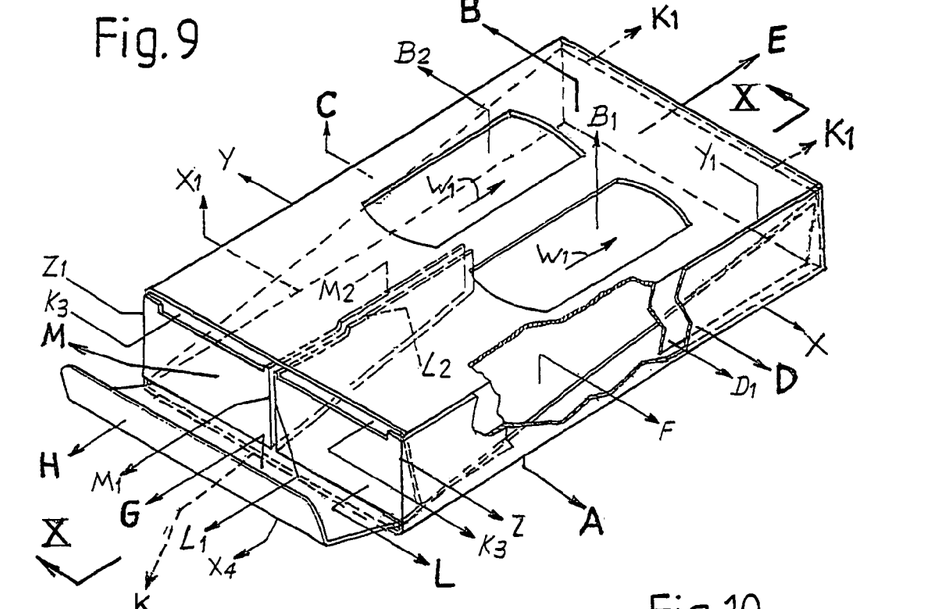
FIG. 9 shows another-perspective view in a similar configuration to FIG. 6, with some parts removed.
Figure 10:
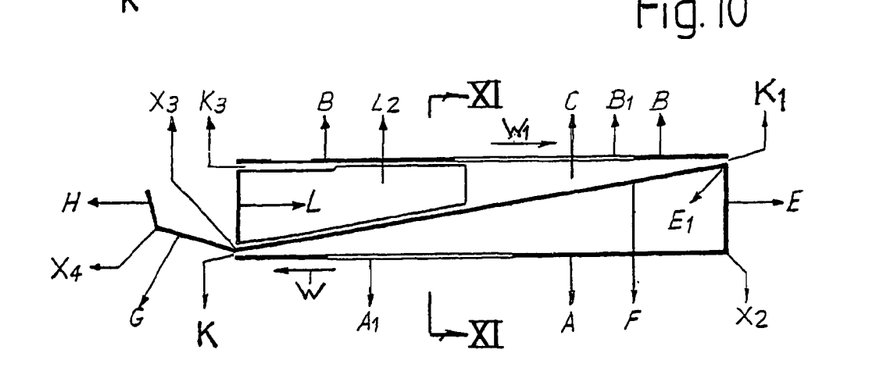
FIGS. 10 and 11 show sections taken from X—X and XI—XI as marked in FIG. 9.
Figure 11:
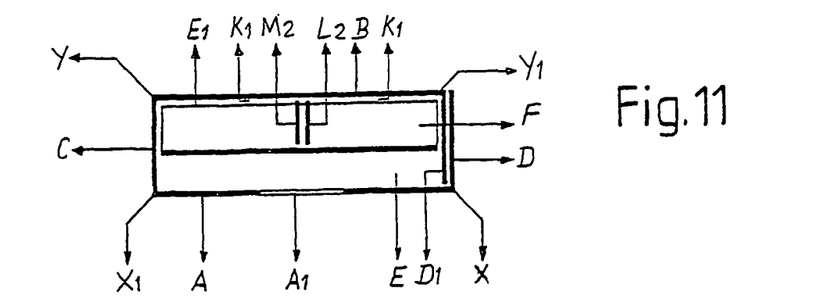

To illustrate how the dispensing carton is erected (this may be automated), FIG. 2 shows the first step in which the separator F is folded toward the interior of the box on the half-cut line E1 so that the separator F touches the inside surface (drawn in small squares) of face A of the carton. Face B is then folded along score line Y (FIG. 3). At this point, side D is folded along score line X (FIG. 4), and glue is applied to the inside of side D along the tab D1. When the carton is set up into its three-dimensional shape, stabilized by the short side E, sets may be inserted (in this case three sets) of bandages (individually wrapped in sachets, usually of paper but also of other materials), in which each set may consist of for example six/eight or more bandages, depending on the dimensions and shape of the dispensing container and on the dimensions of the various types of bandages (or other objects). These bandages—or the like—can be inserted from the side G end which is kept open, into the internal spaces defined between the separator F and the faces A and B, behind windows A, B1 and B2. Tabs L and M are then folded along their score lines Z–Z1 and L1–M1 and inserted inside the carton, to fulfill the function of separating the two sets of bandages which, in the illustrative dispensing carton shown here, fit behind the two windows B1 and B2 of face B: the two sets of bandages, separated by tabs L and M, cannot therefore interfere with each other and correct operation with the possibility of choice is therefore possible. As shown in FIG. 5*ff*, once the box is closed by means of the flap H, the dispenser is ready to be used. The user can choose the bandage sitting in the space behind the window A1 (FIG. 7) in face A, or the bandages sitting in the space behind window B1 or window B2, both of which are formed in face B. FIGS. 7 and 8 and FIG. 10 show clearly that, by pushing with a finger through one of the windows A1 or B1 or B2, it is possible to push the bandage P along the sloping surface formed by the separator F and out (one at a time) of the slot K, for bandages behind window A1, with sliding direction W; or out of slot K1 in the case of bandages corresponding to window B1 or window B2 in face B, with sliding direction W1. Slot K is formed along the edge between score line X3 and face A, while slot K1 is formed along the edge between score line E1 and face B (see in particular FIG. 10). The slots K and K1 are both suited to the thickness of the bandage or other objects which they are designed to release. Slot K (for one-at-a-time removal of bandages visible in window A1) and slot K1 (for one-at-a-time removal of bandages visible in windows B1 and B2) are created as a result of the correct erection of the dispensing container, the measurements and dimensions of which are such as to form precisely these narrow slots between sides A and G, and sides B and E, respectively, so that the bandage can be removed even though the dispensing container is firmly closed on all sides. Slots K3 formed between face B and the extensions L, M are for inserting the tab H, which thus completes the closure of the carton. Slots K and K1 remain available for removal of products as and when required when the latter are acted upon through the slots A1 or B1 or B2.

At the end of the process (which can be mechanized in accordance with paper conversion methods), the result is dispensing cartons of a variety of shapes and dimensions, made of paper, paperboard or other materials, with an internal separator F forming a sloping surface relative to both of the major faces A and B, on which separator F, when the carton is erected and glued, the bandages or other products can slide. The resulting dispensing container thus allows the user to remove the bandage (or other object) contained in the carton) one at a time by acting through the windows A1 or B1 or B2 without having to open and close the carton, unlike the packages currently on the market.

The optional presence of the two tabs M and L which are specially made the right shape and length, and are folded along their respective score lines and inserted inside the carton, serves to keep the sets of bandages separate from each other, in the case in which there are two windows in the face, such as face B, of the packaging, in such a way that the two types of bandage (or other object) cannot in any way become muddled with each other.

It will be understood that the drawing shows only an example purely as a practical demonstration of the invention, and that the invention can be varied in its shapes and arrangements without thereby departing from the scope of the concept on which the invention is based. The presence of any reference numbers in the appended claims is for the purpose of facilitating the reading of the claims with reference to the description and drawing, and does not limit the scope of protection represented by the claims.

The invention claimed is:

1. A parallelepiped-shaped carton made of paperboard or the like for packaging and dispensing products such as adhesive bandages for small wounds, tongue depressors, protective covers for monaural or binaural stethoscopes, spatulas and cervical brushes for gynecological use and other, usually individually wrapped objects, the carton comprising:
   a first and a second main faces;
   two long sides, wherein one face or side of said main faces and said long sides forming a tab for the gluing of the carton;
   a first short side/edge forming a first end wall;
   a second short side/edge forming a second end wall opposite said first end wall; and
   a separator extending in an internal volume of the carton from said first end wall to said second end wall and forming a linear sloping surface and being aligned with one of said two main faces, said separator dividing said internal volume of the carton when folded, into a first seat for the products between said separator and said first main face; and a second seat for the products between said separator and said second main face, wherein on each of said two main faces there is formed at least one window; said first short side and said second short side are connected to said separator along a first and a second folding lines and at the end of said separator, a closing wall is formed opposite to said short edge and provided with a closing flap and opposite dispensing slots, through which an individual product can be slid out by a force acting on the product through said window, are defined between each of said two main faces and the corresponding first and second folding lines.

2. A parallelepiped-shaped carton made of paperboard or the like for packaging and dispensing products such as adhesive bandages for small wounds, tongue depressors, protective covers for monaural or binaural stethoscopes, spatulas and cervical brushes for gynecological use and other, usually individually wrapped objects, the carton comprising:
- a first and a second main faces,
- two long edges wherein one face or side of which is extended by a flap for the gluing of the carton;
- a short edge forming a first end wall; and
- a separator forming a slipping linear sloping surface extending in an internal volume of the carton from said short edge and being aligned with one of said two main faces, said separator dividing said internal volume of the carton when folded, into a first and a second seats between said separator and said corresponding main faces wherein on each of said two main faces there is formed at least one window, said first short side and said second short side are connected to said separator along a first and a second folding lines and at the end of said separator, a closing wall is formed opposite to said short edge and provided with a closing flap and sideway of said short edge, the said long edges are without closing appendixes, whereas from the opposite edges of said long edges, foldable appendixes stretch out adjacent a set of opposite dispensing slots, through which an individual product can be slid out by a force acting on the product through said window, are defined between each of said two main faces and the corresponding ends of said separator.

3. A carton as claimed in claim 1, wherein on one of said two main faces, two adjacent windows are provided, and a set of foldable appendixes are extended by foldable portions inwardly of the seat defined between said main face and said separator, to form a divider in order to subdivide said seat into two separate spaces to which two windows are made to correspond.

4. A carton as claimed in claim 1, wherein on at least one of said main faces, two adjacent windows are and an internal divider is formed between said two windows, so as to form two separate spaces for different products to be pushed out through a slot.

5. A carton as claimed in claim 4, wherein said internal divider consists of two extensions extending from two opposite edges perpendicular to said two faces and to first of two said slots, which extensions are folded along the wall of the carton contiguous with said first slot and also having continuations to form said internal divider and define said two separate spaces.

6. A carton as claimed in claim 1, wherein said separator is produced as a continuation of one of two said faces at right angles to said slots.

7. A carton as claimed in claim 2, wherein on one of said two main faces, two adjacent windows are provided, and said foldable appendixes are extended by foldable portions inwardly of the seat defined between said main face and said separator, to form a divider in order to subdivide said seat into two separate spaces to which said two windows are made to correspond.

8. A carton as claimed in claim 2, wherein on at least one of said main faces, two adjacent windows are provided and an internal divider is formed between said two windows, so as to form two separate spaces for different products to be pushed out through said slot.

9. A carton as claimed in claim 4, wherein on another of said main faces, two additional adjacent windows are provided and another internal divider is formed between the two additional adjacent windows, so as to form two separate spaces for different products to be pushed out through said slot.

10. A carton as claimed in claim 2, wherein said separator is produced as a continuation of one of said two faces at right angles to said slots.

11. A carton as claimed in claim 3, wherein said separator is produced as a continuation of one of said two faces at right angles to said slots.

12. A carton as claimed in claim 8, wherein said internal divider consists of two extensions extending from two opposite edges perpendicular to said two faces and to first of two said slots, which extensions are folded along the wall of the carton contiguous with said first slot and also having continuations to form said internal divider and define said two separate spaces.

13. A carton according to claim 1, wherein said carton is made of a cardboard material.

14. A carton according to claim 2, wherein said carton is made of a cardboard material.

* * * * *